United States Patent

Ganaja et al.

[11] Patent Number: 6,125,574
[45] Date of Patent: Oct. 3, 2000

[54] FISHING LINE FASTENER

[75] Inventors: Scott O. Ganaja, San Luis Obispo; Nicholas M. Grisaffi, Rancho Santa Margarita; Paul White, San Clemente, all of Calif.

[73] Assignee: The NoKnots Group, Incorporated, Santa Margarita, Calif.

[21] Appl. No.: 09/044,962

[22] Filed: Mar. 19, 1998

Related U.S. Application Data

[63] Continuation of application No. 08/650,831, May 20, 1996, abandoned.

[51] Int. Cl.[7] ............................ A01K 91/04; A01K 91/03
[52] U.S. Cl. ............................ 43/43.1; 43/44.9; 43/44.93; 24/136 L
[58] Field of Search ................... 43/43.1, 44.91, 43/44.9, 44.93, 44.92, 44.95, 44.88, 44.89; 24/136 K, 136 L

[56] References Cited

U.S. PATENT DOCUMENTS

| | | | |
|---|---|---|---|
| 1,547,746 | 7/1925 | Gore | 43/44.91 |
| 2,214,961 | 9/1940 | Hawley | 43/44.93 |
| 2,379,676 | 7/1945 | Blackstone | 43/44.93 |
| 2,444,791 | 7/1948 | Stahnke | 43/44.93 |
| 2,504,241 | 4/1950 | Wulff | 43/44.91 |
| 2,570,293 | 10/1951 | Vandrais | 43/44.91 |
| 2,890,510 | 6/1959 | Spalding | 43/44.93 |
| 3,084,470 | 4/1963 | Heater | 43/44.91 |
| 3,096,599 | 7/1963 | Baron | 43/44.9 |
| 3,628,279 | 12/1971 | Halone | 43/44.9 |
| 4,644,681 | 2/1987 | Hutson | 43/44.93 |
| 5,345,657 | 9/1994 | Shimizu | 24/136 L |
| 5,666,699 | 9/1997 | Takahashi | 24/136 L |

*Primary Examiner*—Kurt Rowan
*Attorney, Agent, or Firm*—Lariviere, Grubman & Payne, LLP

[57] ABSTRACT

An improved fishing line fastening device comprising a pair of mating members with a first one of the members being formed with a central opening extending therethrough and the other of the members being formed with a projection tapered inwardly and downwardly at an angle in excess of about 10° and being extendable through the opening of the first member and carrying flange means at the tip of the projection for securing the members together.

4 Claims, 4 Drawing Sheets

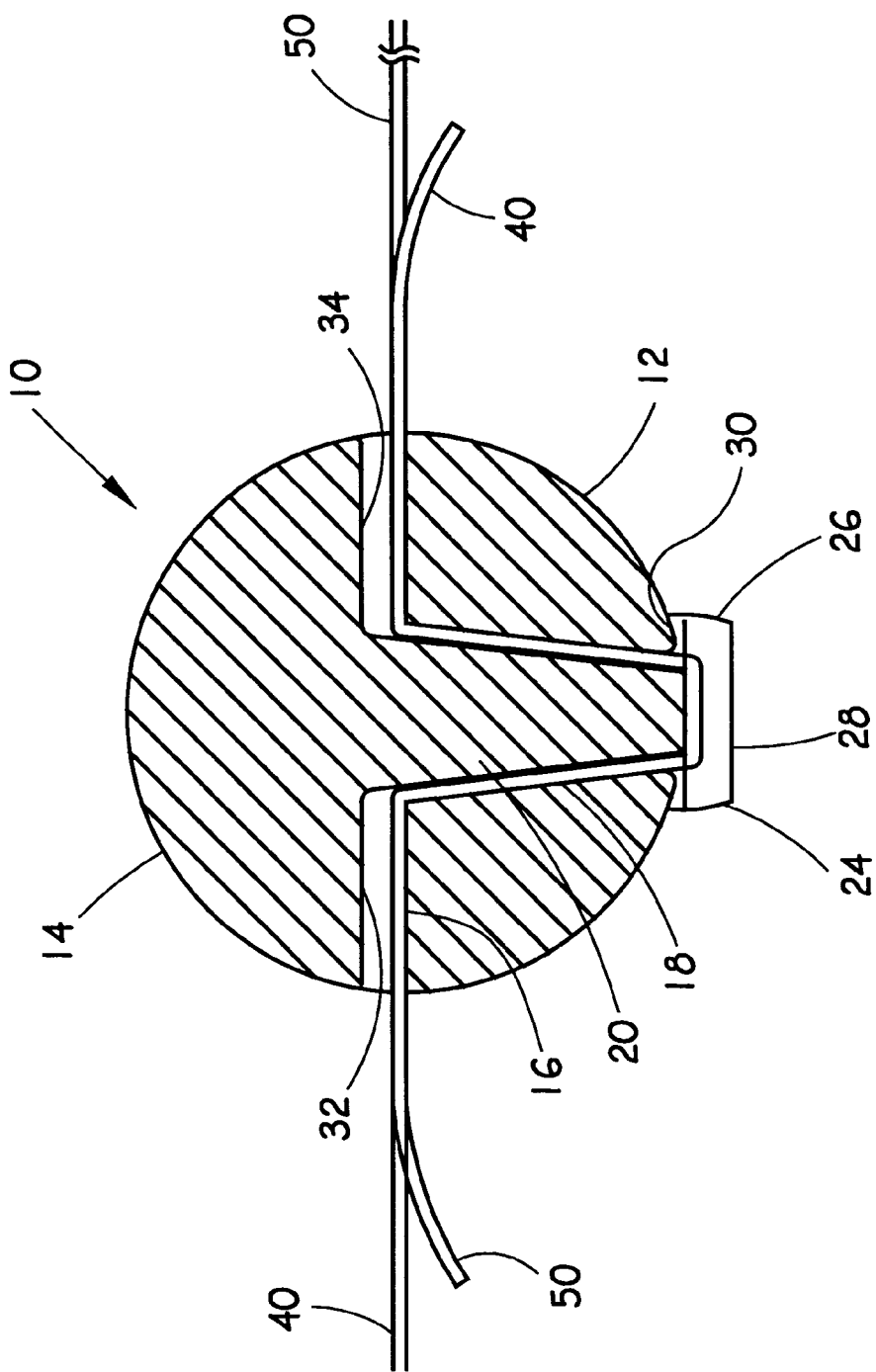

FISHING LINE FASTENER

This is a continuing Patent Application of application Ser. No. 08/650,831, filed May 20, 1996 now abandoned. This continuing Application incorporates by reference application Ser. No. 08/650,831, and contains no new matter. This application hereby claims priority based on U.S. application Ser. No. 08/650,831.

FIELD OF INVENTION

This invention relates to fishing equipment and is particularly directed to improved fishing line fasteners having tapered coupling members for strongly joining two lines and for attaching hooks, flies, sinkers, floats and the like to a fishing line.

PRIOR ART

Non-commercial fishing has been a primary means of obtaining food for thousands of years and has been a popular sport for almost as long. Within the general category of fishing, are many different types of fishing, such as fresh water fishing, fly fishing, surf fishing, deep sea fishing and game fishing. However, all of these types rely, basically, upon use of a fishing line attached to a pole. On the other hand, the characteristics of the fishing line and pole vary considerably, depending upon the particular type of fishing. Also, depending upon the particular type of fishing, various accessories, such as hooks, flies, sinkers, floats and the like, may be attached to the fishing line. Various devices have been proposed for attaching such accessories to the fishing line. However, prior art fishing line fastening devices have been complex to use and expensive to purchase. Also, it has been found that considerable stress is applied to the attached devices which often causes them to become disconnected form the fishing line and, hence, to be ineffective. Thus, many prior art fishing line fastening devices have been ineffective or have been subject to failure in a manner which results in loss of the accessory. However, some accessories, such as flies, may be quite expensive, making their loss a matter of some concern. A search in the United States Patent Office has revealed the following:

| U.S. PAT. NO. | INVENTOR | ISSUED |
| --- | --- | --- |
| 2,379,676 | S. R. Blackstone | July 3, 1945 |
| 2,444,791 | L. R. Stahnke et al | July 6, 1948 |
| 2,764,838 | H. C. Singer | Oct. 2, 1956 |
| 2,881,552 | E. J. Miller | Apr. 14, 1959 |
| 3,091,050 | P. H. Metzler | May 28, 1963 |
| 3,197,914 | R. V. Beverly | Aug. 3, 1965 |
| 3,293,792 | C. E. Bittaker, Jr. | Dec. 27, 1966 |
| 4,235,037 | J. W. Sivertsen | Nov. 25, 1980 |
| 4,893,433 | C. J. Scheffler et at | Jan. 16, 1990 |
| 5,031,351 | H. Rogel | Jul. 16, 1991 |

Each of these references is subject to the disadvantages discussed above. Thus, none of the prior art fishing line fastening devices have been entirely satisfactory.

BRIEF SUMMARY AND OBJECTS OF INVENTION

These disadvantages of the prior art are overcome with the present invention and an improved fishing line fastening device is provided which is simple, inexpensive to purchase and easy to use, but which positively and securely attaches a desired accessory to a fishing line.

These advantages of the present invention are preferably attained by providing an improved fishing line fastening device comprising a pair of mating members, with a first one of the members being formed with a tapered central opening extending therethrough and the other of the members being formed with a projection tapering inwardly and downwardly at an angle in excess of about 10° and being extendable through the opening of the first member and carrying locking flange means at the tip of the projection for securing the members together. and for singificantly increasing the clamping pressure of the members without significantly increasing the pressure required to lock the members together.

Accordingly, it is an object of the present invention to provide an improved fishing line fastening device.

Another object of the present invention is to provide an improved fishing line fastening device which is simple and inexpensive to purchase and use.

An additional object of the present invention is to provide an improved fishing line fastening device which positively and securely attaches a desired accessory to a fishing line or to connect two lines together.

A specific object of the present invention to provide an improved fishing line fastening device comprising a pair of mating members, with a first one of the members being formed with a tapered central opening extending therethrough and the other of the members being formed with a projection which is tapered inwardly and downwardly at an angle in excess of about 10° and being extendable through the opening of the first member and carrying locking flange means at the tip of the projection for releasably securing the members together.

These and other objects and features of the present invention will be apparent from the following detailed description, taken with reference to the figures of the accompanying drawing.

BRIEF DESCRIPTION OF THE DRAWING

FIG. 4 is a diagrammatic representation showing two fishing lines being held together by the fastening device of FIG. 1.

DETAILED DESCRIPTION OF THE INVENTION

Figure 1:
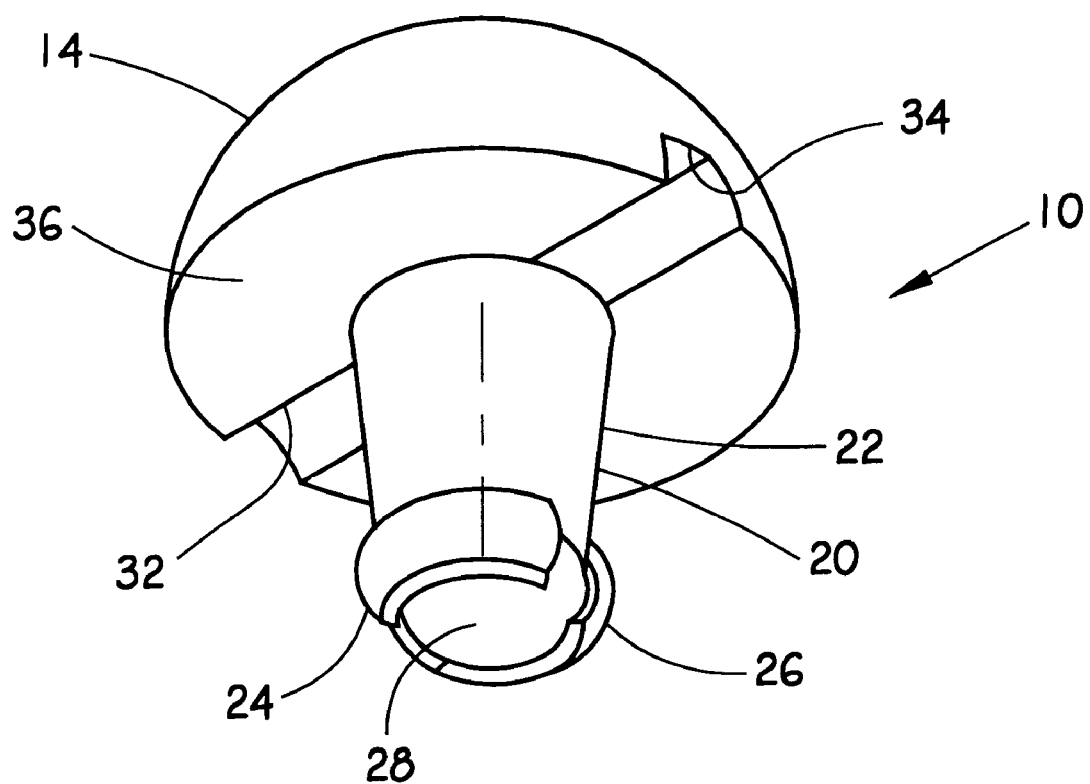
FIG. 1 is an exploded view of a fishing line fastening device embodying the present invention.
Figure 1:
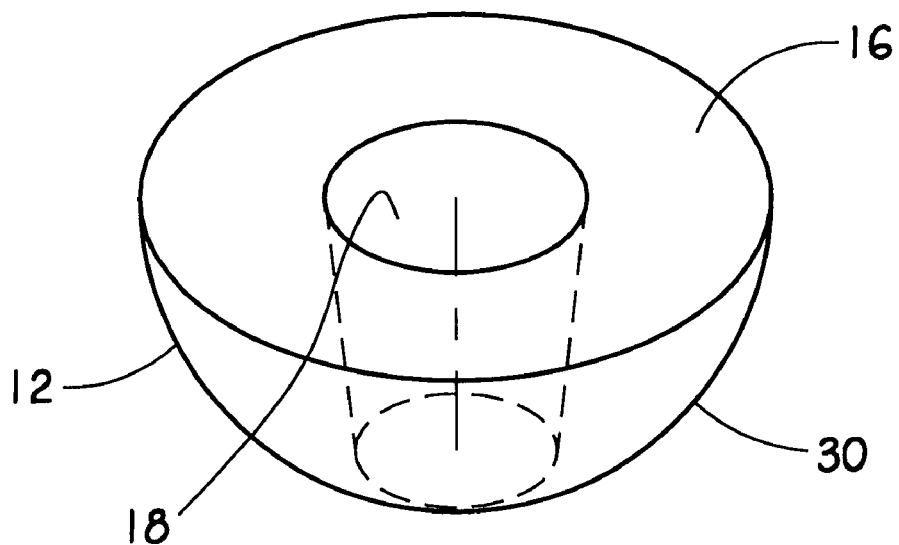
Figure 2:
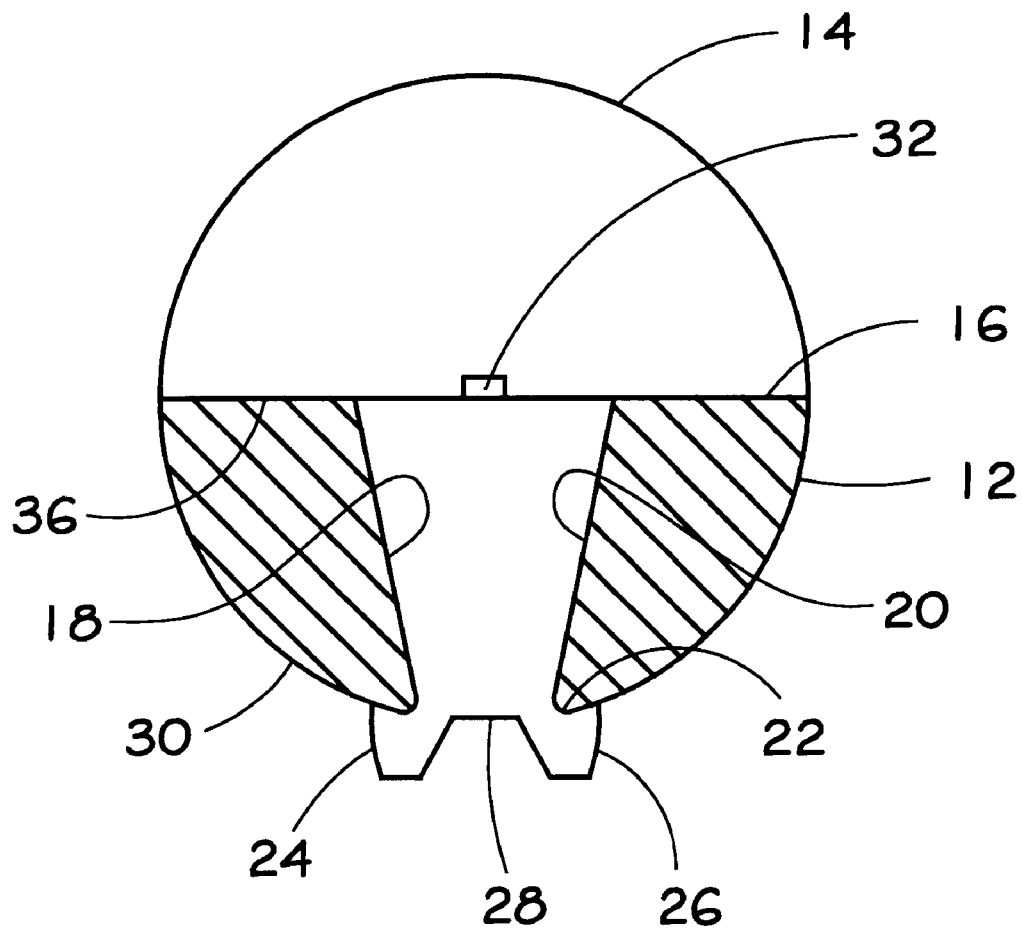
FIG. 2 is a vertical section through the fishing line fastening device of FIG. 1.

In that form of the present invention chosen for purposes of illustration in the drawing, FIG. 1 shows a fishing line fastening device, indicated generally at 10, having a pair of mating members 12 and 14. Member 12 has a flat upper surface 16 and is formed with a central opening 18 which is tapered and extends entirely through the member 12. Member 14 is formed with a central projection 20 which is tapered inwardly and downwardly at an angle in excess of about 10° to mate with the opening 18 of member 12 and is insertable into the opening 18 of member 12 to extend completely through the member 12, as best seen in FIG. 2. The projection 20 is dimensioned to frictionally fit within the opening 18 such that a fishing line is wedged between the outer wall of the projection 20 and the inner wall of opening 18. It has been found that the tapered mating serves to significantly increase the pressure which is applied to clamp a fishing line between the members 12 and 14 without substantially increasing the amount of pressure required to connect the members 12 and 14 together. At the free end 22 of the projection 20 are a pair of outwardly projecting resilient flanges 24 and 26 separated by a central recess 28. As best seen in FIG. 2, the resilient flanges 24 and 26 must be squeezed toward each other in order to pass through opening 18 and, upon projecting out of the opposite end of opening 18, will spring outward to engage the outer surface 30 of the member 12 and to attach member 14 and member 12 together. As shown, a pair of recesses 32 and 34 are provided extending diametrically across the flat undersurface 36 of member 14 and, if desired, similar recesses, not shown, could be provide extending down the sides of the projection 20 to communicate the recesses 32 and 34 with recess 28 at the lower end of the projection 20. Alternatively, if desired, recesses, not shown, could be provided on member 12 adjacent the opening 18.

Figure 3:
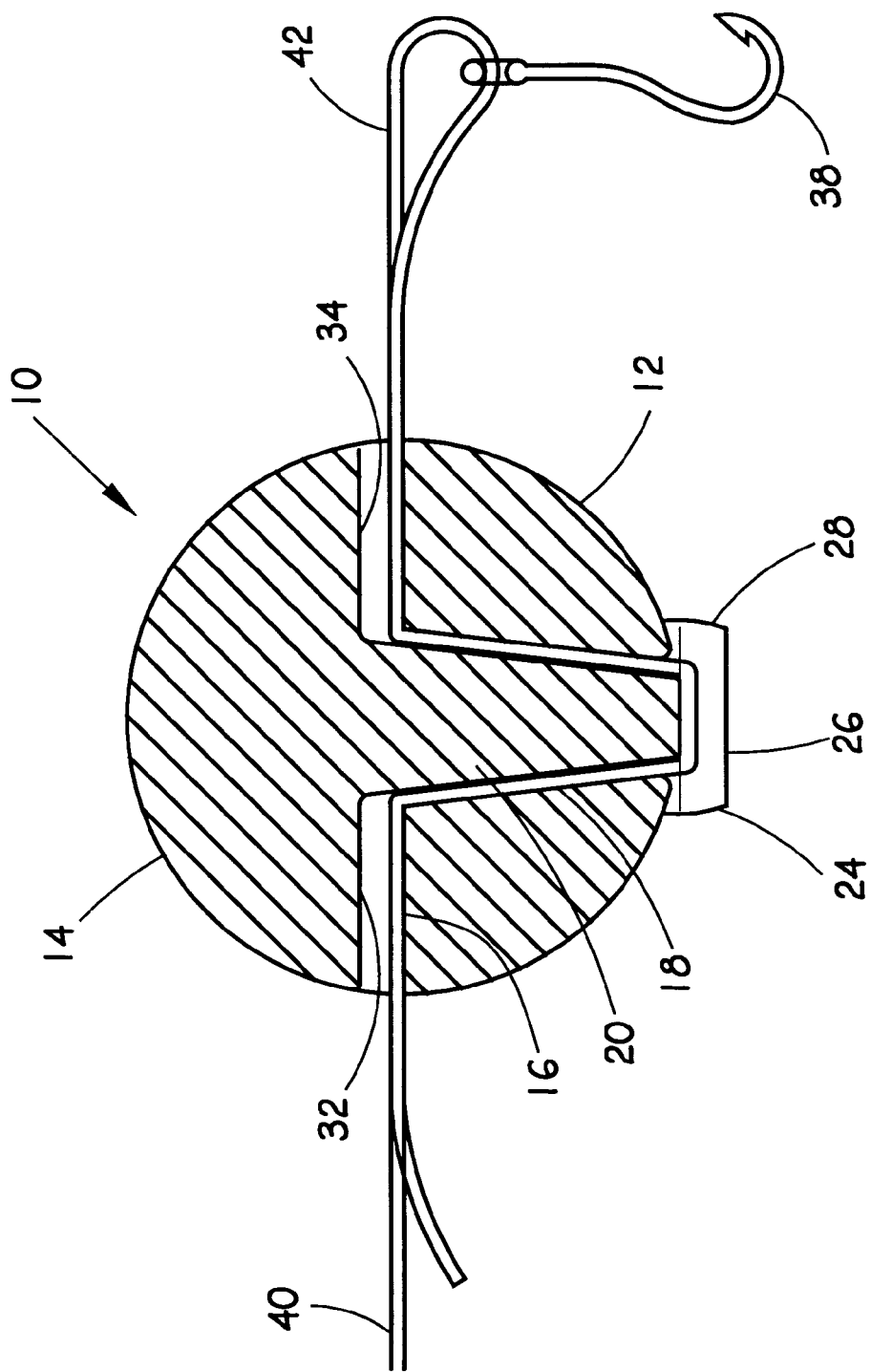
FIG. 3 is a diagrammatic representation showing an accessory attached to a fishing line by means of the fastening device of FIG. 1.

In use, an appliance, such as the hook seen at 38 in FIG. 3, is slid onto a fishing line 40 to a desired position and a loop is made in the fishing line 40 at that position, as seen at 42. The parallel portions of the fishing line 40 forming the ends of the loop 42 are placed into recess 28 at the free end 22 of projection 20 of member 14 of the fishing line fastening device 10. Next, the tapered projection 20 is inserted through opening 18 of member 12 until the resilient flanges 24 and 26 underlie and engage the outer surface 30 of member 12. Because the projection 20 is tapered inwardly and downwardly at an angle in excess of about 10°, this firmly and effectively clamps the fishing line 40 between the members 12 and 14 and, especially, due to the wedging action occurring between projection 20 and the walls of the opening 18. Thus, loop 42 is fixedly established and the hook 38 is fixedly attached to the fishing line 40 at the desired position.

FIG. 4 shows the fastening device 10 as used to attach a plurality of fishing lines 40, 50 together. Both lines 40, 50 are overlapped and set in the central recess 28. The projection 20 of the male member 14 is slid into the opening 18 of the female member 12 until the flanges 24, 26 snap in place behind the outer surface (or shoulder) 30 of the female member 12 to secure the two mated members 12, 14 together. The fishing lines 40, 50 are secured by the interference fit between the outer wall of the projection 20 and the inner wall of the opening 18. The fishing lines 40, 50 pass through the recesses of the male member 32, 34.

Obviously, although the device of the present invention has been described above for use in attaching items to fishing lines, it will be apparent to those skilled in the art that the device can also be used for attaching tow lines to each other or for use with other types of line, rope, wire, cable and the like. In addition, numerous other variations and modifications can be made without departing from the spirit of the present invention. Therefore, it should be clearly understood that the form of the present invention described above and shown in the figures of the accompanying drawing are illustrative only and are not intended to limit the scope of the present invention.

What is claimed is:

1. A fastener for fastening a fishing accessory to a fishing line comprising:

a male member having a flat under surface and a central projection extending therefrom, said projection having a free end and a proximal end, the proximal end of said central projection being centered on the flat under surface;

the free end of said projection having a pair of flanges divided by a central recess;

a female member having a flat upper surface and an opening extending through said female member, said opening being centered on the flat upper surface and being used for inserting the projection of said male member to interlock said male and female members together providing an interference fit, said flanges extending beyond said opening to engage an outer surface of the female member when assembled, wherein the flat under surface and the flat upper surface are parallel to one another; and said interference fit capable of securing a loop in a fishing line, said fishing line passing through said central recess.

2. The fastener of claim 1 wherein said male member has recesses on either side of said projection, said recesses being parallel to the flat upper surface of the female member.

3. A fastener as in claim 1 wherein said interference fit is capable of securing a plurality of fishing lines, and wherein the flat upper surface and the flat under surface mate to form a spherical component.

4. A fastener as in claim 1 wherein said interference fit secures a fishing accessory on a fishing line, and wherein the flange comprises a curved inside surface.

* * * * *